(12) United States Patent
Brown

(10) Patent No.: US 7,905,888 B2
(45) Date of Patent: Mar. 15, 2011

(54) APPARATUS FOR INSERTING FLEXIBLE MEDICAL IMPLANT

(76) Inventor: David C. Brown, Fort Myers, FL (US)

(\*) Notice: Subject to any disclaimer, the term of this patent is extended or adjusted under 35 U.S.C. 154(b) by 592 days.

(21) Appl. No.: 11/707,491

(22) Filed: Feb. 16, 2007

(65) Prior Publication Data
US 2008/0200922 A1    Aug. 21, 2008

(51) Int. Cl.
*A61F 9/00*        (2006.01)
(52) U.S. Cl. ........................................ 606/107
(58) Field of Classification Search .............. 623/6.12, 623/907, 6.38, 6.43; 606/107, 103
See application file for complete search history.

(56) References Cited

U.S. PATENT DOCUMENTS

| 5,425,734 | A  | * | 6/1995 | Blake ........................... 606/107 |
| 6,283,975 | B1 |   | 9/2001 | Glick et al. |
| 7,156,854 | B2 |   | 1/2007 | Brown et al. |
| 2002/0193805 | A1 | * | 12/2002 | Ott et al. ........................ 606/107 |
| 2005/0065534 | A1 | * | 3/2005 | Hohl ............................ 606/107 |
| 2006/0036262 | A1 |   | 2/2006 | Hohl |
| 2007/0000801 | A1 |   | 1/2007 | Mauran et al. |

\* cited by examiner

*Primary Examiner* — Anhtuan T Nguyen
*Assistant Examiner* — Tin Nguyen
(74) *Attorney, Agent, or Firm* — Claude E. Cooke, Jr.; John J. Love; Burleson Cooke LLP

(57) ABSTRACT

A device for injecting flexible implants, such as an implantable collamer lens (ICL) is disclosed. In a preferred embodiment it includes, a chamber in which the implant is placed, an injection tube through which the implant will pass, the chamber and tube forming a channel along which is a guide.

9 Claims, 6 Drawing Sheets

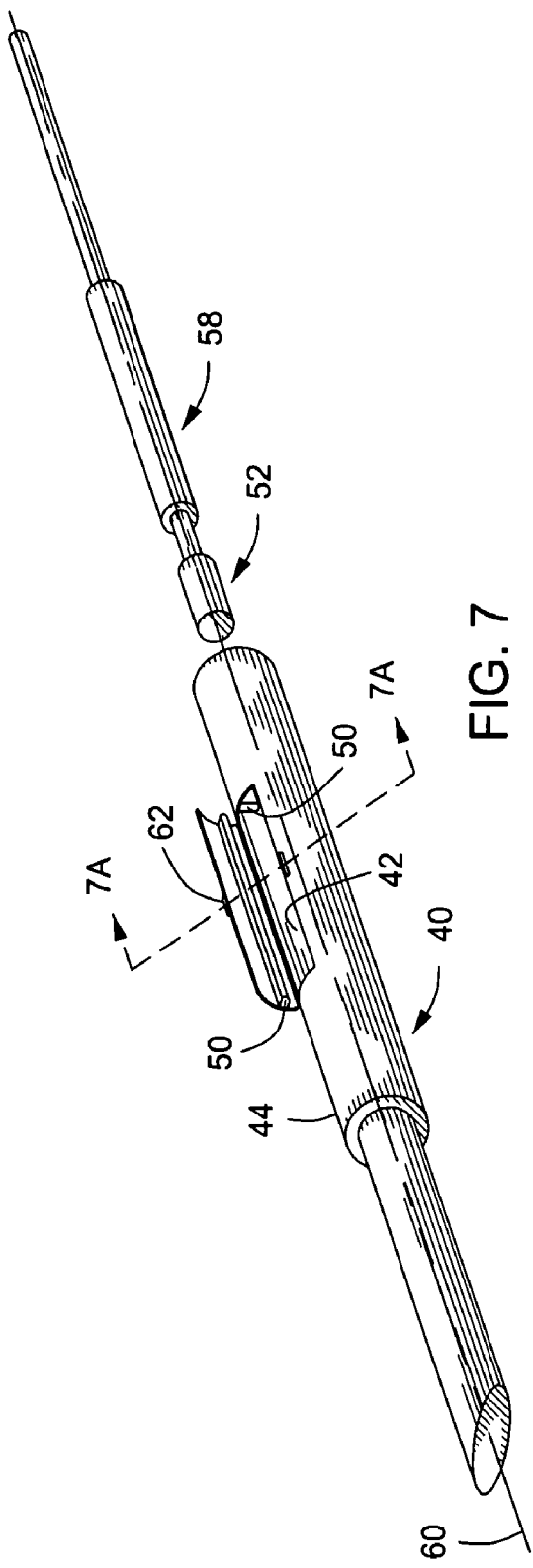
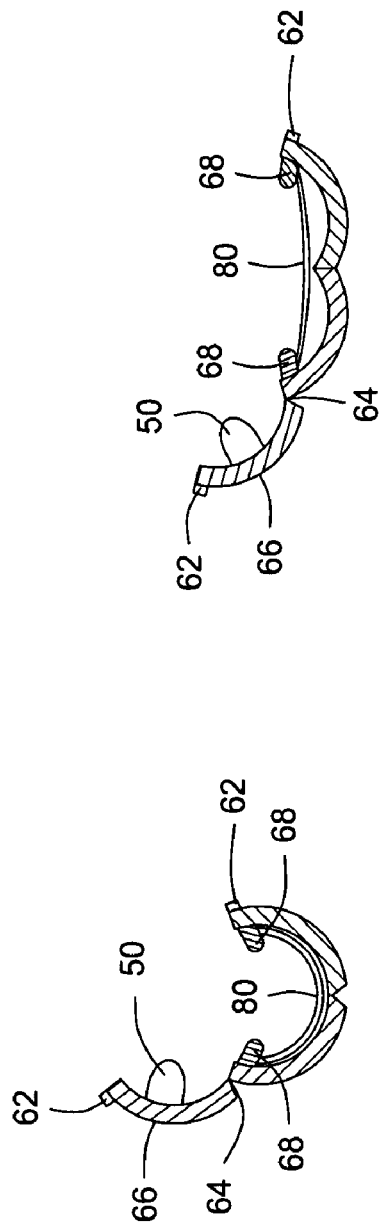

APPARATUS FOR INSERTING FLEXIBLE MEDICAL IMPLANT

BACKGROUND OF THE INVENTION

1. Field of the Invention

This application relates to surgical devices. More particularly, it relates to a method and apparatus for folding and injecting deformable devices, such as an artificial lens into an eye.

2. Background of the Invention

For various reasons, such as cataract or injury, the natural lens of an eye may need replacement or the refractive state of the eye changed by injecting optical devices into the eye. Synthetic lenses for replacement or refractive error modification are available from various manufacturers, who make the lens to the required optical characteristics. For example, intraocular lenses ("IOL") are often used in treating cataract patients. Implantable contact lenses ("ICL") may be used to treat myopia (nearsightedness), myopia with astigmatism, hyperopia, and hyperopia with astigmatism.

If the implanted lens or other device is rigid, a relatively large incision is required to accommodate the lens. The use of a flexible lens or other device allows the lens or other device to be rolled or folded and inserted through a smaller incision. The flexible lens or other device is folded, inserted into the eye, and allowed to unfold in position in the patient's eye.

If the flexible lens or other device is implanted with an injector, as opposed to the use of an instrument such as forceps, the size of the incision may be further reduced. A small incision is made in the cornea or sclera through which a small tube, part of the injector, is inserted. The rolled or folded lens or other device is pushed through the injector tube and opens inside the eye.

FIG. 1 shows the basic structure of an eye. Eye 20 has natural lens 10, which is partially exposed at pupil 12 underneath cornea 14. Around pupil 12 is iris 16. Lens 10 is attached to ciliary body 18 within sclera 22. Other tissue, such as choroid 24, retina 26, and fovea 28 are also present. Finally, optic nerve 30 carries optical signals from eye 20 to the brain.

For various reasons, such as cataract or injury, the natural lens of an eye may need replacement. Synthetic lenses for replacement are available from various manufacturers, who make the lens to the required optical characteristics. For cataract surgery, a small incision is made at the junction of cornea 14 and sclera 22. Once the cataract has been pulverized and removed, a soft, folded IOL is inserted through the incision and placed into the lens capsule 10. For ICL or other device implantation, a small incision is made in cornea 14 or sclera 22 and the lens is inserted behind iris 16 through pupil 12 in front of natural lens 10. With a flexible lens and a lens injector, these incisions may be less than 3 mm long and close without use of sutures.

One example of an injector is found in U.S. Pat. No. 6,283,975 B1. The lens is placed in the load chamber of an inserter in an unfolded position. The inserter is then folded which results in the lens also being folded. The load chamber is then placed in an injector and the lens is pushed out of the load chamber into the recipient with a plunger.

Because the lens or other device is not held in place while being pushed out, it may rotate inside the injector and unfold in the wrong orientation (e.g., backwards or inverted). This may also occur if the lens or other device is not properly oriented in the injector before insertion. Rotation may also cause the lens or other device to unfold improperly or incompletely. Improper placement of the lens, which can be difficult to detect, can cause distorted vision or loss of implant effectiveness and increase the likelihood of the recipient developing cataracts or other adverse affects. If any of these problems are detected, the incision must be enlarged so that the lens may be removed and correctly positioned. Thus, there is a need in the art for an injector that can consistently and reliably insert a lens or other device in the proper orientation.

SUMMARY OF INVENTION

The disclosed device includes an apparatus for injecting a flexible medical implant. In a preferred embodiment, the device includes an injector cartridge with an injector cartridge and injection tube in communication therewith. A flexible medical implant is placed within the injector cartridge and passes down a channel formed by the injector cartridge and injection tube and enters the recipient in a rolled or folded position. The folded implant is prevented from rotating relative to the axis of the channel by a guide extending down the length of said channel. The injector cartridge may be placed in an injector for use or may be used with a plunger or plunger assembly.

The disclosed method includes the use of the disclosed device or one similar thereto. The flexible medical implant is placed into the device. The implant may be folded and then placed into the device or placed in the device and folded afterward. The implant is then passed down a channel through an injection tube into the recipient. If the implant was unfolded upon placement in the device, it may be folded prior to or simultaneously with the step of passing it down the channel into the recipient.

BRIEF DESCRIPTION OF THE DRAWINGS

FIG. 7 is a perspective view of one embodiment of the invented injector cartridge and a plunger that may be used therewith. FIG. 7A is a cross-sectional view of one embodiment of the injector cartridge. FIG. 7B is a cross-sectional view of one embodiment of the injector cartridge.

DETAILED DESCRIPTION OF THE PREFERRED EMBODIMENT

Figure 1:
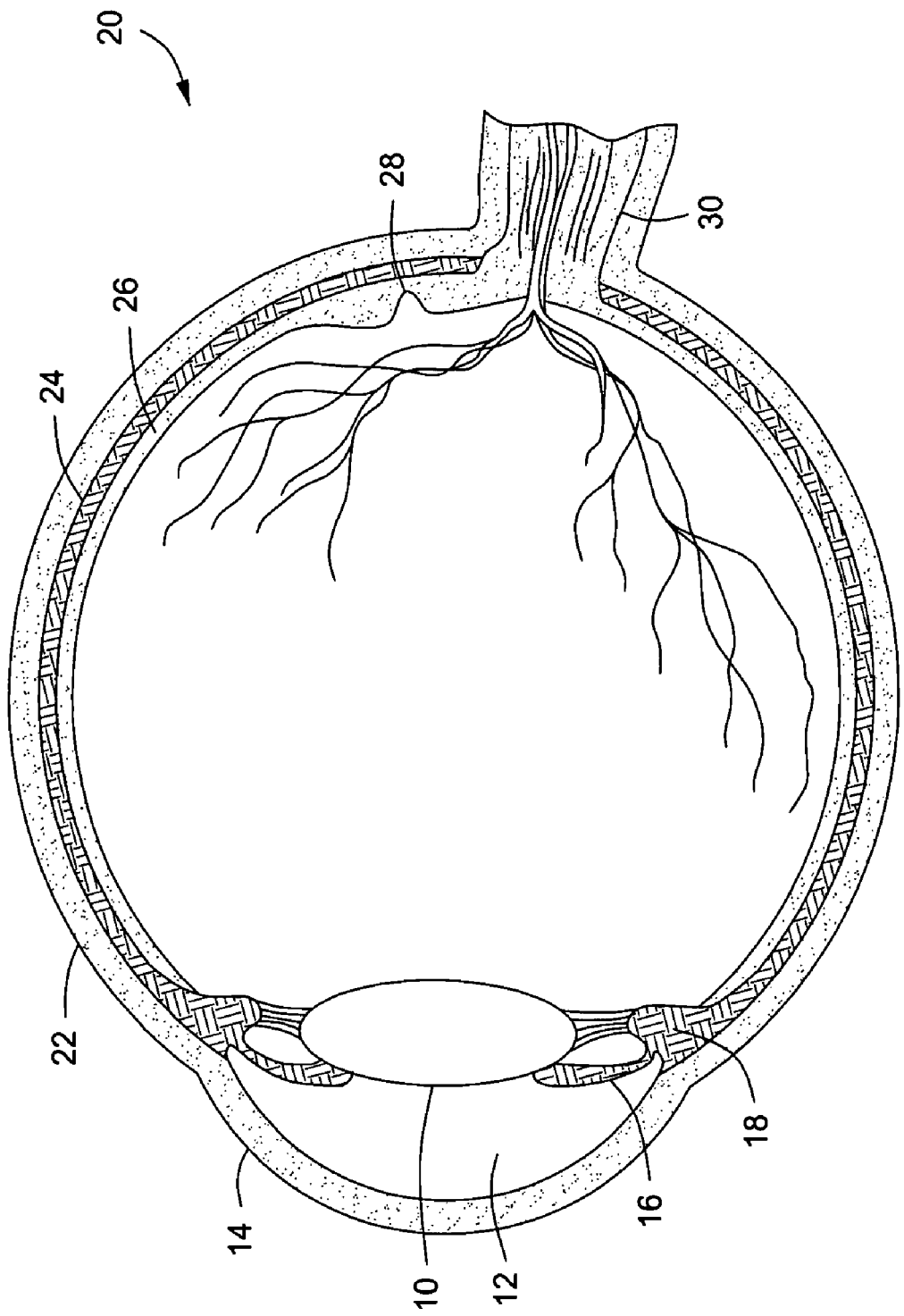
FIG. 1 is an illustration of an eye.

Referring now to the drawings, the details of exemplary embodiments of the present invention are schematically illustrated. Like elements in the drawings will be represented by like numbers. The preferred embodiment is described in connection with the insertion of implantable lens in an eye, but the principles involved may be adapted to the insertion of other flexible implants for other purposes by one skilled in the art.

Figure 2:
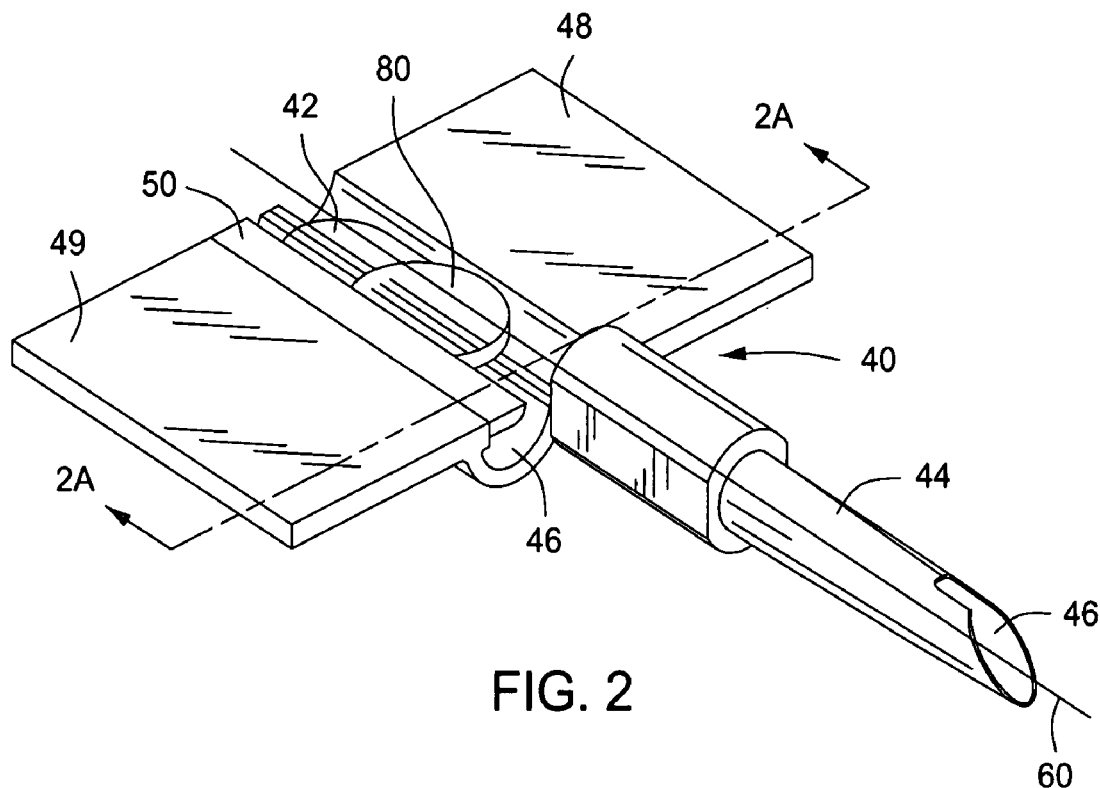
FIG. 2 is a perspective view of one embodiment of the injector cartridge in an open position.
Figure 2A:
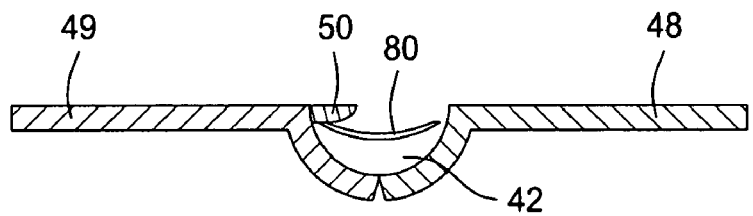
FIG. 2A is a cross-sectional view of one embodiment of the injector cartridge in an open position.
Figure 2B:
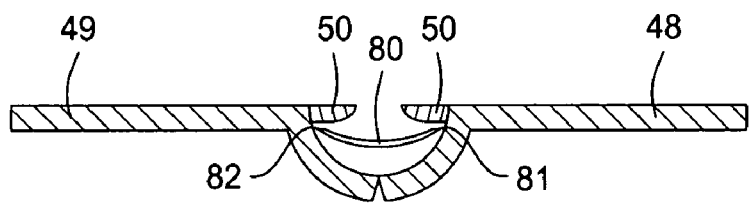
FIG. 2B is a cross-sectional view of one embodiment of the injector cartridge in an open position.
Figure 3:
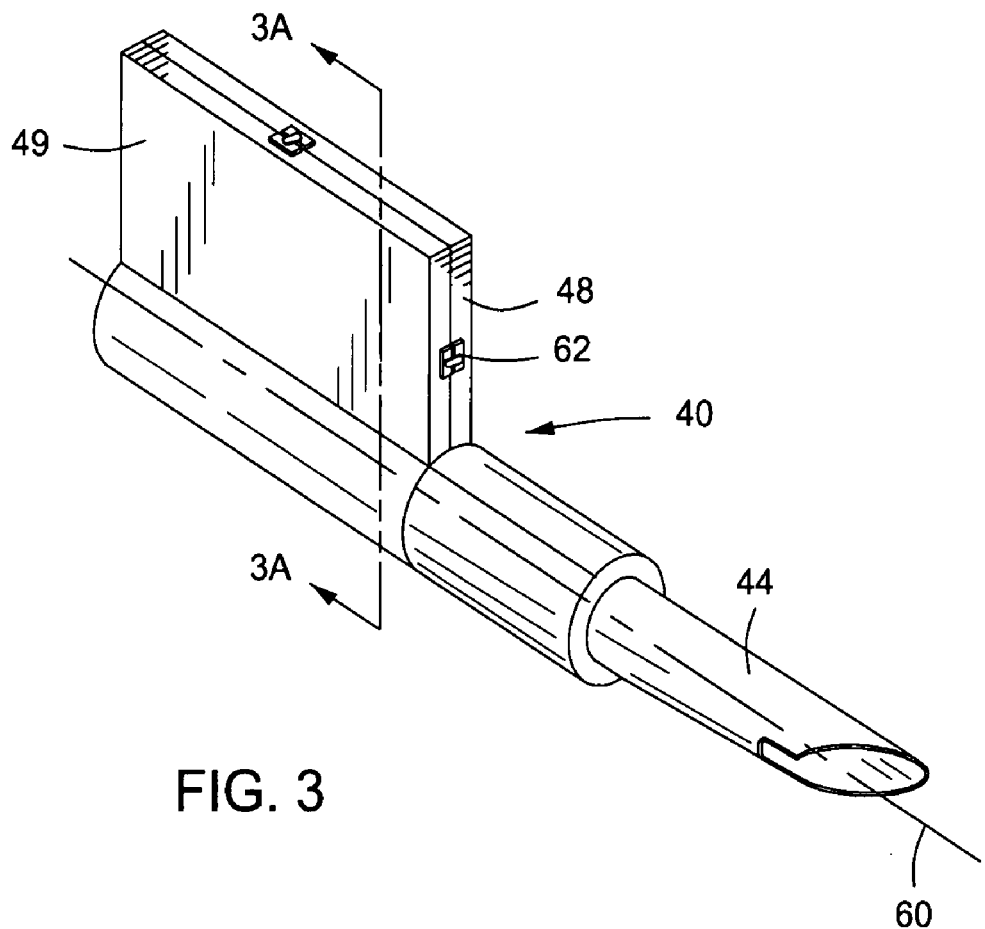
FIG. 3 is a perspective view of one embodiment of the injector cartridge in a closed position.
Figure 3A:
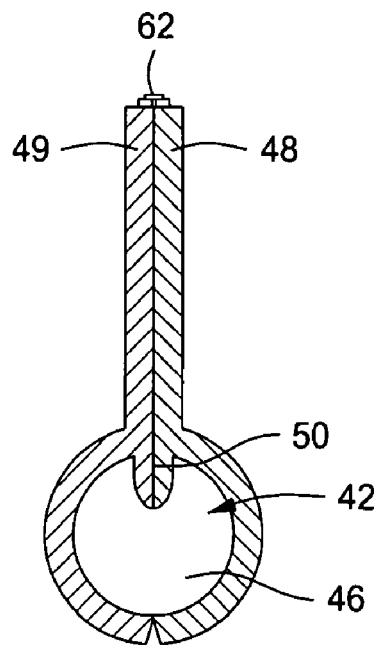
FIG. 3A is a cross-sectional view of one embodiment of the injector cartridge in a closed position.

FIG. 2 shows one embodiment of the disclosed injector cartridge in an open position. Flexible medical implant 80 is placed in chamber 42. As shown in FIG. 2, the injector cartridge is generally a tubular member having two segments pivoted to each other along a longitudinal axis. Wings 48 and 49 extend outwardly from the segments. As shown in FIGS. 2A and 2B, implant 80 is placed so that its edge is located under guide 50. When injector cartridge 40 is closed, as shown in FIG. 3, implant 80 is preferably folded. As shown in FIG. 3A, guide 50 then extends downward into chamber 42 and edges 81 and 82 of implant 80 are aligned on each side of guide 50. This prevents implant 80 from rotating around longitudinal axis 60. Guide 50 extends into injection tube 44. Chamber 42 and injection tube 44 form channel 46 through which plunger 52 and implant 80 pass. In one embodiment, latch 62 is used to keep injector cartridge 40 closed once implant 80 is placed therein. Latch 62 may be located anywhere on injector cartridge 40 where it may fulfill the function of holding injector cartridge 40 closed. In an alternative embodiment, injector cartridge 40 is designed to bias it to the open position when wings 48 and 49 are pulled apart and/or to bias to the closed position when wings 48 and 49 are brought into proximity with one another.

The preferred guide 50 is shown located at the both edges of chamber 42, as shown in FIGS. 2B and 3A, and wings 48 and 49 as this location is optimal for folding implant 80 around guide 50 without excessive handling of implant 80. This configuration also reduces the risk of implant 80 being caught between wings 48 and 49 and damaged during folding. However, guide 50 may be located at only one edge or elsewhere in chamber 42 and remain within the scope of the invention. The preferred guide also has the advantage of holding implant 80 in place during folding. The preferred shape for guide 50 is an elevated ridge with a rounded top, as shown in the drawings, but other shapes may be desirable for reasons, such as reduced manufacturing cost, and are within the scope of the disclosed apparatus and methods. Guide 50 may also be of different sizes—e.g., wider and/or longer—to fill more or less of the space in chamber 42 and/or channel 46. Guide is preferably substantially straight for ease of use, but other configurations are possible within the scope of the disclosed apparatus and methods.

Figure 4:
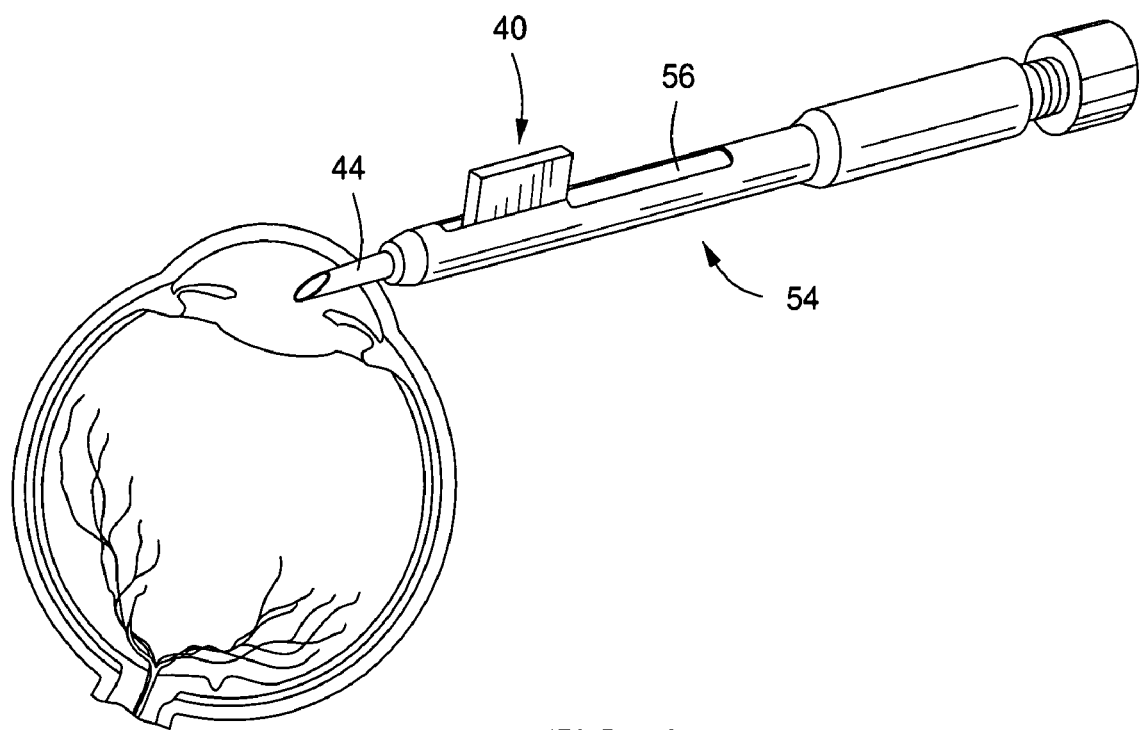
FIG. 4 is a perspective view of one embodiment of the injector cartridge in a closed position in an insertion device.
Figure 5:
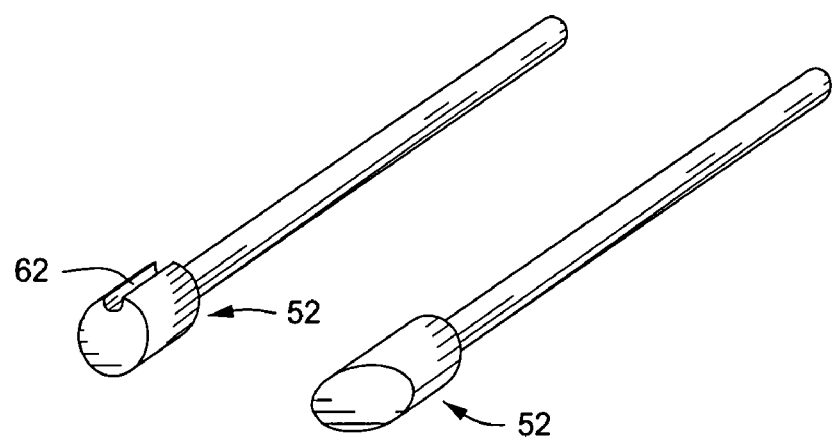
FIG. 5 is a perspective view of two embodiments of a plunger that may be used with the injector cartridge.

In one embodiment, injector cartridge 40 may be held in injector 54, an example of which is shown in FIG. 4. If an injector 54 is used, injector cartridge 40 is placed in receiving slot 56 and held in a closed position. Injector 54 includes plunger 52 which is aligned with injector cartridge 40 and chamber 42 along longitudinal axis 60. Plunger 52 is used to move implant 80 along guide 50 out of chamber 42 through injection tube 44 into recipient. As shown in FIG. 5, plunger 52 may include groove 62 that is shaped to fit around guide 50 or may have any other shape that allows it to push implant 80 into recipient.

Figure 6:
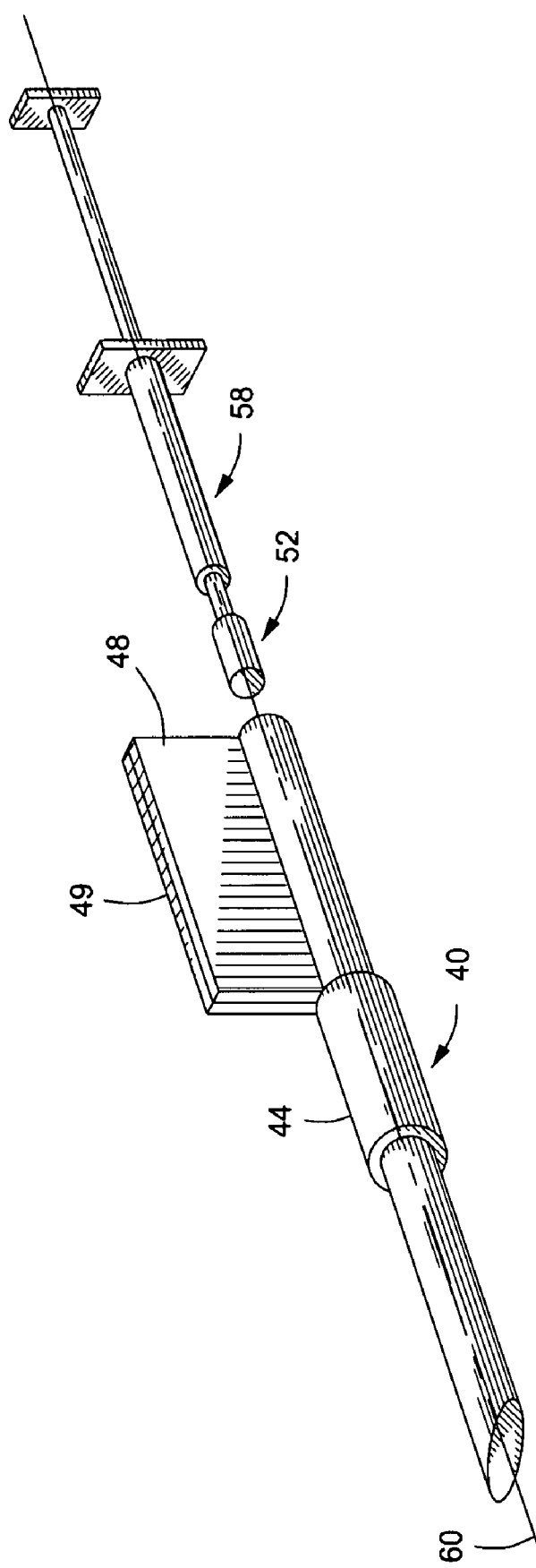
FIG. 6 is a perspective view of one embodiment of the injector cartridge and a plunger assembly that may be used therewith.

Alternatively, injector cartridge 40 may be held closed by hand or by latch 62 and used with plunger assembly 58, an example of which is shown in FIG. 6. Plunger 52 is aligned with injector cartridge 40 and chamber 42 along longitudinal axis 60. Plunger 52 is used to move implant 80 along guide 50 out of chamber 42 through injection tube 44 into recipient. Plunger 52 may be mated to fit around guide 50 or may have any other shape that allows it to push implant 80 into recipient.

FIG. 7 shows another embodiment of injector cartridge 40. Chamber is accessed by opening lid 66, which may be connected by hinge 64 or may separate completely from injector cartridge 40. As shown in FIG. 7A, flanges 68 are positioned to either side of implant 80 and preferably near the edge of the opening created by opening lid 66. Flanges 68, which may be included in other embodiments, help keep implant 80 in place during the process of closing lid 66. As shown in FIG. 7B, there is preferably a pivot point at or near the bottom of injector cartridge 40. Injector cartridge 40 is opened and loaded with implant 80 being placed between flanges 68. Injector cartridge 40 is then flexed to the proper position for closing, which is the position where lid 66 can be closed and latch 62 closed.

Alternatively, folding of implant 80 may be accomplished by gradually narrowing channel 46 along which implant 80 passes such that implant 80 is folded as it travels down channel 46 to recipient.

Implant 80 may be shipped in place in injector cartridge 40 or may be shipped separately. If implant 80 is shipped with injector cartridge 40, they are preferably immersed in saline solution. This eliminates or significantly reduces the need to handle implant 80 as part of the implantation process, which in turn reduces the risk of complications such as infection.

Although the present invention has been described with reference to specific details, it is not intended that such details should be regarded as limitations on the scope of the invention, except as and to the extent that they are included in the accompanying claims.

I claim:

1. An injector cartridge for use in an injector device for implanting a flexible medical device comprising:
   a tubular member having first and second segments integrally hinged to each other along a longitudinal axis;
   a chamber formed within the tubular member having a circular cross sectional shape;
   a guide extending inwardly from one of the segments, wherein the guide comprises a ridge extending into the device injector cartridge and injection tube substantially parallel to the longitudinal axis of the flexible medical device; and
   an injection tube communicating with the chamber.

2. The apparatus of claim 1 wherein the injector cartridge further comprises a wing extending from each of the first and second segments.

3. The apparatus of claim 2 wherein the guide is located between the chamber and one of the wings when the device is open and extends into the chamber at least when the device is closed.

4. The apparatus of claim 1 further comprising an injector with a receiving slot shaped to receive and retain the device injector cartridge.

5. The apparatus of claim 1 further comprising a plunger having a groove shaped to fit around the guide when the plunger is inserted into the injector cartridge or injection tube.

6. The apparatus of claim 1 wherein the chamber and/or injection tube are shaped such that the device is folded as it moves through the injector body or injection tube.

7. The apparatus of claim 1 wherein the flexible medical device is a lens.

8. The device of claim 1 wherein the guide includes two portions, each having a planar surface and a rounded surface:
   the portions extending inwardly from opposite sides of the tubular segments when in an open position;
   the planar surfaces contacting each other when the device is in a closed position, the two rounded surfaces joining to form a smooth rounded surface at the most radially inwardly point of the guide.

9. The device according to claim 1 wherein the hinge is located at the inner surface of the tubular segments.

* * * * *